United States Patent [19]

Boghen et al.

[11] Patent Number: 5,010,056
[45] Date of Patent: Apr. 23, 1991

[54] PHARMACEUTICAL COMPOSITION FOR INTRANASAL ADMINISTRATION, COMPRISING GH-RELEASING HORMONE, A CHOLINERGIC AGONIST AND OPTIONALLY A BILE SALT

[75] Inventors: Franklin M. Boghen, Gambolò; Franco Camanni, Turin; Piero Del Soldato, Monza; Ezio Ghigo, Turin; Eugenio Müller, Milan, all of Italy

[73] Assignee: Pierrel Spa, Italy

[21] Appl. No.: 223,378

[22] Filed: Jul. 25, 1988

[30] Foreign Application Priority Data

Jul. 30, 1987 [IT] Italy ............................. 21513 A/87

[51] Int. Cl.[5] .................. A61K 37/02; A61K 9/06; A61K 9/12; A61K 9/14

[52] U.S. Cl. ....................... 514/12; 424/43; 424/45; 424/46; 424/489; 424/499; 514/937; 514/938; 514/944; 514/964; 514/965

[58] Field of Search .............. 514/12, 937, 938, 944, 514/964, 965; 424/43, 45, 46, 489, 499

[56] References Cited

U.S. PATENT DOCUMENTS 4,613,500  9/1986  Suzuki et al. ............... 514/951
4,663,318  5/1987  Davis .......................... 514/215
4,818,531  4/1989  Anderson et al. ........... 514/12
4,880,778  11/1989  Bowers et al. ............. 514/12

Primary Examiner—Ronald W. Griffin
Attorney, Agent, or Firm—Parkhurst, Wendel & Rossi

[57] ABSTRACT

A pharmaceutical composition for intranasal administration comprising GHRH, a cholinergic agonist and in case a bile salt, suitable for the treatment of growth disorders and for use in the diagnosis of GH hypophyseal functionality.

11 Claims, 4 Drawing Sheets

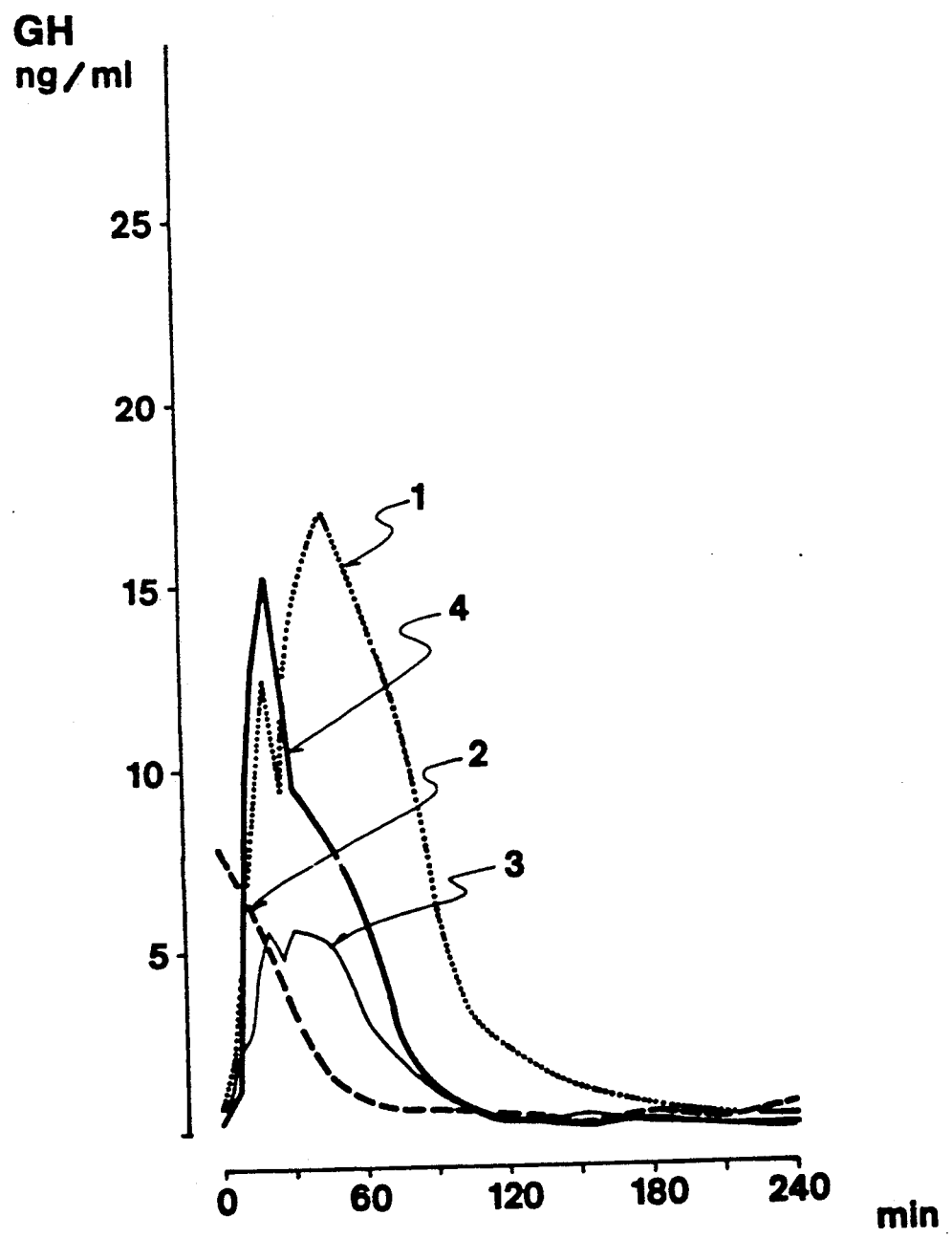

PHARMACEUTICAL COMPOSITION FOR INTRANASAL ADMINISTRATION, COMPRISING GH-RELEASING HORMONE, A CHOLINERGIC AGONIST AND OPTIONALLY A BILE SALT

This invention relates to a pharmaceutical composition for intranasal administration comprising GH-releasing hormone (GHRH), a cholinergic agonist and in case a bile salt, the term "cholinergic agonist" meaning either a cholinomimetic substance with direct action or an anticholinesterase agent.

More particularly, the present invention relates to a pharmaceutical composition for intranasal administration comprising GHRH, a cholinergic antagonist and in case a bile salt and suitable excipients, which is suitable for treatment and/or diagnosis of growth disorders or for other therapeutic and diagnostic indications in which GH is involved.

PRIOR ART

The identification and characterisation of the hypothalamic GHRH which controls in the stimulatory sense the release of the somatotrope GH from the hypophysis has in recent years determined considerable progress in the treatment of growth disorders of endocrinic nature and in the diagnosis of the functionality of the hypophysis on stimulation by GHRH.

In this respect it has been found that most subjects affected by low GH secretion are able to respond to GHRH stimulus not at the hypophyseal cell but at the hypothalamic structures responsible for GHRH production (Evuan-Brion D., "Neuroendocrine Perspectives", E. E. Muller and R. M. McLeod eds, vol. 5 pp 101-109-Elsevier Amsterdam 1986).

The chronic administration of GHRH therefore represents in these cases a more rational treatment than the conventional treatment with GH.

The effectiveness of GHRH administration, either for treatment or diagnostic purposes, is hindered in particular by the inhibition of GH release by the other hypothalamic hormone, namely somatostatin (Wehrenberg W. B. et al., "Annu. Rev. Toxicol. Pharmacol." 25, 463-483, 1985).

It has however been found that previous activation of the cholinergic system potentiates the response of GH to the administration of GHRH, probably by blocking the release of somatostatin.

It has been found in particular that the previous administration of an oral dose of pyridostigmine is able to stimulate GH secretion and significantly increase the effect of intravenously injected GHRH.

It is however well known that the biovailability of orally administered pyridostigmine is low, as in the case of all substances with a quaternary nitrogen atom (P. Taylor in "The Pharmacological Basis of Therapeutics", A. Goodman Gilman, L. S. Goodman, T. W. Rall and F. Murad eds. p. 118, Macmillan Pub. Co. 1985).

GHRH was also administered nasally (Evans W. S. et al. "J. Clinic. Endocr. Metabol." 6, 846, 1985). However the authors observed that in nasal administration the bioavailability of GHRH is low so that very high doses are required, of up to 300-1000 times the parenteral doses, to obtain comparable effects.

SUMMARY OF THE INVENTION

The present invention provides a pharmaceutical composition for intranasal administration suitable for the treatment of growth disorders and the diagnosis of hypophyseal functionality, comprising therapeutically effective quantities of GHRH, a cholinergic agonist and in case a bile salt, together with pharmaceutically acceptable non-toxic excipients for intranasal administration.

On intranasal administration of said composition, the relative active principles have high bioavailability. Moreover, said composition acts synergically and thus its use considerably potentiates the GH release effect obtainable by the separate administration of the individual components.

In addition, a considerable advantage is that intranasal administration is much more acceptable both for the doctor and for the patient in that it produces no pain and no cutaneous reactions, and is easier to carry out.

DETAILED DESCRIPTION OF THE INVENTION

Figure 1:
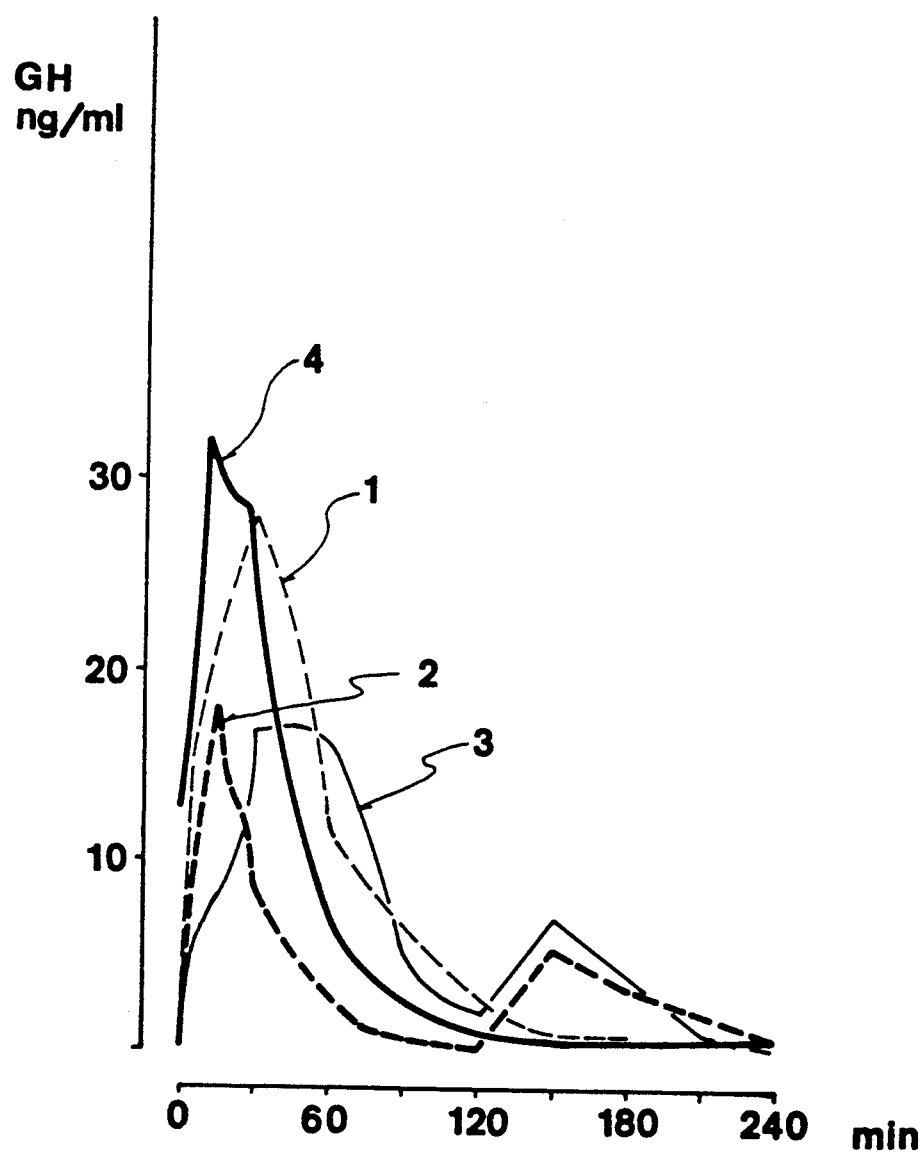

The composition comprising GHRH according to the invention can be prepared using various types of cholinergic agonists and in case bile salts. It can also be prepared in various forms.

The following cholinergic agonists can be used:

choline esters such as methacholine chloride, carbachol chloride, bethanecol chloride;

natural and synthetic alkaloids such as arecholine, pilocarpine, muscarine, acyclidine, oxotremorine;

reversible anticholinesterase agents such as physostigmine, neostigmine, edrophonium, pyridostigmine, demecarium, ambenonium.

The bile salts can be the alkaline salts of glycocholic, glycochenodeoxycholic, taurocholic, taurochenodeoxycholic, deoxycholic, chenodeoxycholic, ursodeoxycholic or glycodeoxycholic acid. The bile salt contributes to improving nasal absorption.

In addition to the GHRH, the cholinergic agonist and in case the bile salt, the composition according to the invention can contain one or more non-toxic pharmaceutically acceptable excipients.

The choice of excipients depends not only on the chemical and physical characteristics of the active principles and required posology but also on the desired type of composition.

The composition of the invention can be prepared in the form of a suspension, ointment, cream, solution, gel, sustained release gel, droplets, atomised spray or aerosol. The composition can also be prepared as a powder.

Compatible with its nature and complexity, the composition is preferably isotonic.

Aqueous-based excipients and those containing halogenated hydrocarbon-based propellants tend to accelerate the absorption rate.

Excipients based on gelled matrices or oil/water or water/oil emulsions used for intranasal application either directly or by atomisation enable more prolonged effects to be obtained without significantly penalising the rapidity of these effects.

The dose of the individual components administered varies according to the body weight of the patient and his clinical conditions.

The typical dose of GHRH is from 3 to 60 $\mu g/kg$ of body weight, of cholinergic agonist is from 20 to 100 $\mu g/kg$ and of bile salt is from 10 to 50 $\mu g/kg$, to be administered nasally from one to three times per day.

The quantity of composition necessary for releasing the required dose depends on the concentration of active principles in the composition.

The concentration of active principles varies with the type of composition and lies within the following ranges:

Water-based composition: GHRH from 0.01 to 0.75% by weight; cholinergic agonist from 0.15 to 7.5% by weight.

Composition with halogenated hydrocarbon-based propellants: GHRH from 0.01 to 1.0% by weight; cholinergic agonist from 0.3 to 4.0% by weight.

Composition with gelled matrices or in oil/water or water/oil emulsions: GHRH from 0.2 to 1.5% by weight; cholinergic agonist from 1.5 to 7.5% by weight.

Composition in the form of powder: GHRH from 0.4 to 3% by weight; cholinergic agonist from 3.0 to 15% by weight.

In all cases the bile salt content varies from 0.5 to 5% by weight.

Intranasal administration of said compositions amplifies the somatotropic response to GHRH, so that in therapeutic use the effect on growth is potentiated and in diagnostic use the possibility of evaluating the hypophyseal response is improved.

The following examples of the preparation of compositions according to the invention are given hereinafter for non-limiting illustration only.

EXAMPLE 1

Solution for Intranasal Atomisation

| GHRH | | 0.1 g |
|---|---|---|
| Mannitol | | 10.0 g |
| Distilled water | to make up to | 100 ml |

The mannitol and GHRH are dissolved in the distilled water. The solution is divided equally into 100 vials, frozen and lyophilised.

At the moment of use the solution for intranasal atomisation is prepared by adding to a vial 1 mm of a solution of the following composition:

| Neostimine methylsulphate | | 0.3 g |
|---|---|---|
| Sodium chloride | | 0.8 g |
| Distilled water | to make up to | 100 ml |

The solution is administered by a dispenser or mechanical atomiser of predetermined volume. Said dispenser or atomiser can be used for one or more administrations.

EXAMPLE 2

Solution for Intranasal Atomisation

To obtain a solution suitable for intranasal atomisation, the lyophilised contents of 6 vials of GHRH of Example 1 are dissolved in 3 ml of a solution having the following composition:

| Neostigmine methylsulphate | | 0.3 g |
|---|---|---|
| Sodium glycocholate | | 0.5 g |
| Sodium chloride | | 0.6 g |
| Distilled water | to make up to | 100 ml |

The solution is administered as in Example 1.

EXAMPLE 3

Solution for Intranasal Atomisation

To obtain a solution suitable for intranasal atomisation, the lyophilised contents of 6 vials of GHRH of Example 1 are dissolved in 6 ml of a solution having the following composition:

| Neostigmine methylsulphate | | 0.6 g |
|---|---|---|
| Sodium glycodeoxycholate | | 1.0 g |
| Sodium chloride | | 0.54 g |
| Distilled water | to make up to | 100 ml |

The solution is administered as in Example 1.

EXAMPLE 4

Solution for Intranasal Atomisation (Multidose)

| GHRH | | 1.0 g |
|---|---|---|
| Mannitol | | 10.0 g |
| Distilled water | to make up to | 100 ml |

The mannitol and GHRH are dissolved in the distilled water. The solution is divided equally into 1000 vials and lyophilised.

At the moment of use the solution for intranasal atomisation is prepared by adding to a vial 1 mm of a solution of the following composition:

| Neostigmine methylsulphate | | 1.2 g |
|---|---|---|
| Benzalkonium chloride | | 0.1 g |
| Sodium chloride | | 0.64 g |
| Distilled water | to make up to | 100 ml |

The solution is administered as in Example 1.

EXAMPLE 5

Solution for Intranasal Atomisation (Multidose)

| GHRH | | 0.35 g |
|---|---|---|
| Mannitol | | 5.0 g |
| Distilled water | to make up to | 100 ml |

The mannitol and GHRH are dissolved in the distilled water. The solution is divided equally into 100 vials and lyophilised.

At the moment of use the solution for intranasal atomisation is prepared by adding to a vial 1 mm of a solution of the following composition:

| Neostigmine methylsulphate | | 3.0 g |
|---|---|---|
| Sodium glycodeoxycholate | | 1.0 g |
| Sodium chloride | | 0.14 g |
| Distilled water | to make up to | 100 ml |

The solution is administered by a dispenser or atomiser of predetermined volume. Said dispenser or atomiser can be used for one or more administrations.

EXAMPLE 6

Solution for Intranasal Atomisation

| GHRH | 0.35 g |
|---|---|

| | | |
|---|---|---|
| -continued | | |
| Distilled water | to make up to | 100 ml |

The GHRH is dissolved in the distilled water. The solution is divided equally into 100 vials, frozen and lyophilised.

At the moment of use the solution for intranasal atomisation is regenerated by adding to a lyophilised GHRH vial 1 mm of a solution of the following composition:

| | | |
|---|---|---|
| Neostigmine methylsulphate | | 3 g |
| Sodium chloride | | 0.36 g |
| Distilled water | to make up to | 100 ml |

The solution is administered by a dispenser or atomiser of predetermined volume, which can be used for one or more administrations.

EXAMPLE 7

Example 6 is repeated using 0.7 g of GHRH

EXAMPLE 8

Example 6 is repeated adding 5 g of mannitol to the GHRH solution.

EXAMPLE 9

Pressurised Aerosol for Intranasal Spray

| | |
|---|---|
| GHRH | 0.75 g |
| Neostigmine methylsulphate | 3.00 g |
| Polysorbate 80 | 0.50 g |
| Absolute ethanol | 5.00 g |
| Freon 12/114 | 90.75 g |

The GHRH and neostigmine methylsulphate, previously micronized (ca. 5µ) are dispersed in absolute alcohol, the polysorbate 80 and the propellant are added and the product packaged into aerosol cans. Adminstration is by a dispenser valve set to 50–100 µl per delivery.

EXAMPLE 10

Oily Suspension for Intranasal Instillation

| | | |
|---|---|---|
| GHRH | | 1.0 g |
| Neostigmine methylsulphate | | 3.0 g |
| Medium-chain saturated fatty acid triglycerides | to make up to | 100 ml |

The GHRH and neostigmine methylsulphate are micronized (diameter ca. 5µ) and the active principles are dispersed in the excipient by a colloidal mill. Administration is by intranasal instillation.

EXAMPLE 11

Ointment for Intranasal Application

| | |
|---|---|
| GHRH | 0.75 g |
| Neostigmine methylsulphate | 3.00 g |
| White vaseline | 96.25 g |

The GHRH and neostigmine methylsulphate are micronized (diameter ca. 5µ). The vaseline is melted at 60° C. after which the active principles are incorporated during cooling. The product is applied as a normal ointment for nasal use.

EXAMPLES 12, 13, 14, 15

Example 11 is repeated, but using methacholine chloride, carbachol chloride, pilocarpine and pyridostigmine bromide respectively instead of the neostigmine methylsulphate.

The compositions according to the invention were used in clinical trials conducted on 10 children from eight to ten years old and weighing about 35 kg, and also on a like number of adults weighing about 70 kg.

The programme of said clinical trials was conducted in accordance with the following administration scheme:

1. intravenous administration of 1 µg/kg of GHRH;
2. intranasal administration of 10 µg/kg of GHRH;
3. intranasal administration of 3 mg of neostigmine dissolved in 100 µl of water.
4. intranasal administration of 10 µg/kg of GHRH and 3 mg of neostigmine dissolved in 100 µl of water.

The hematic GH content was determined every 30 minutes from administration until the 240th minute.

Figure 2:
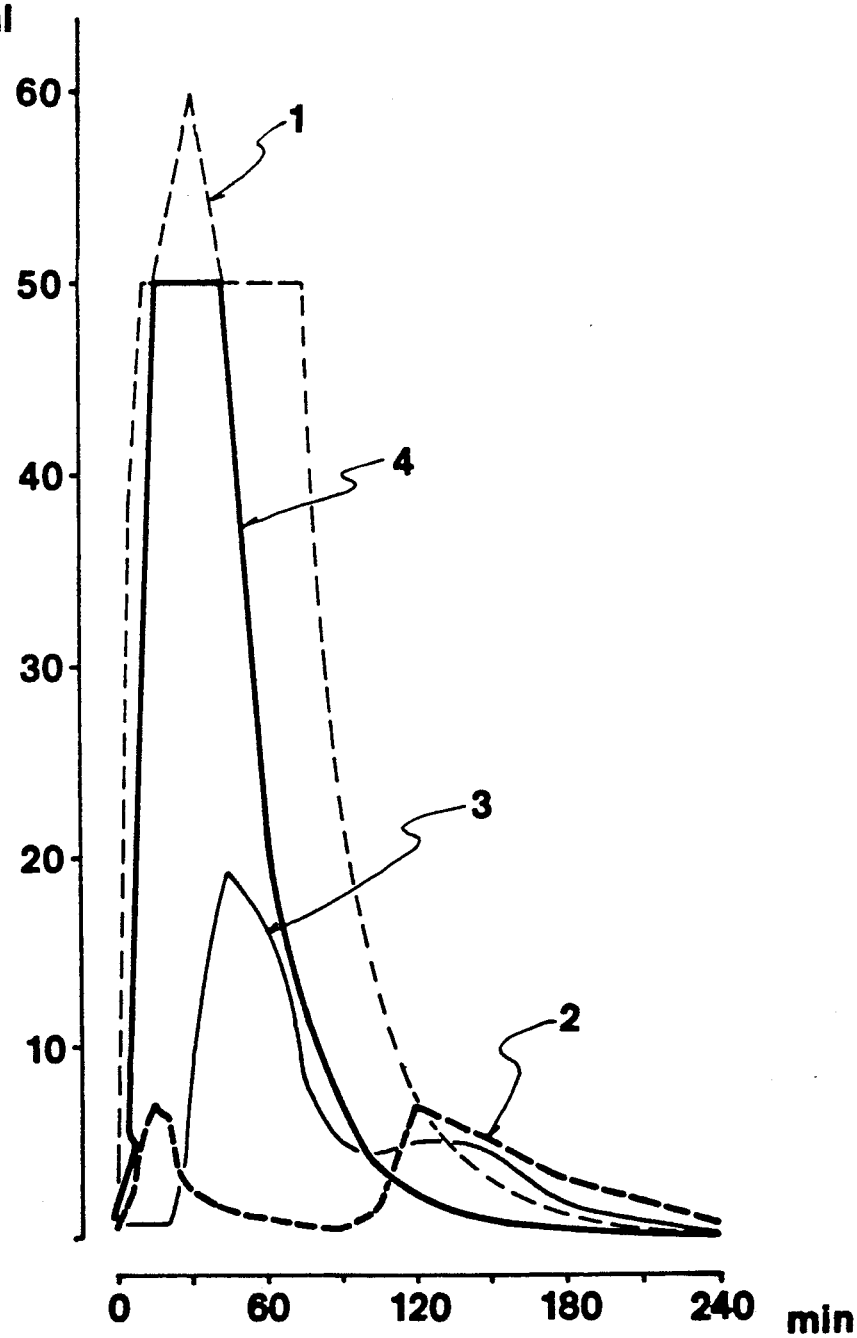
Figure 3:
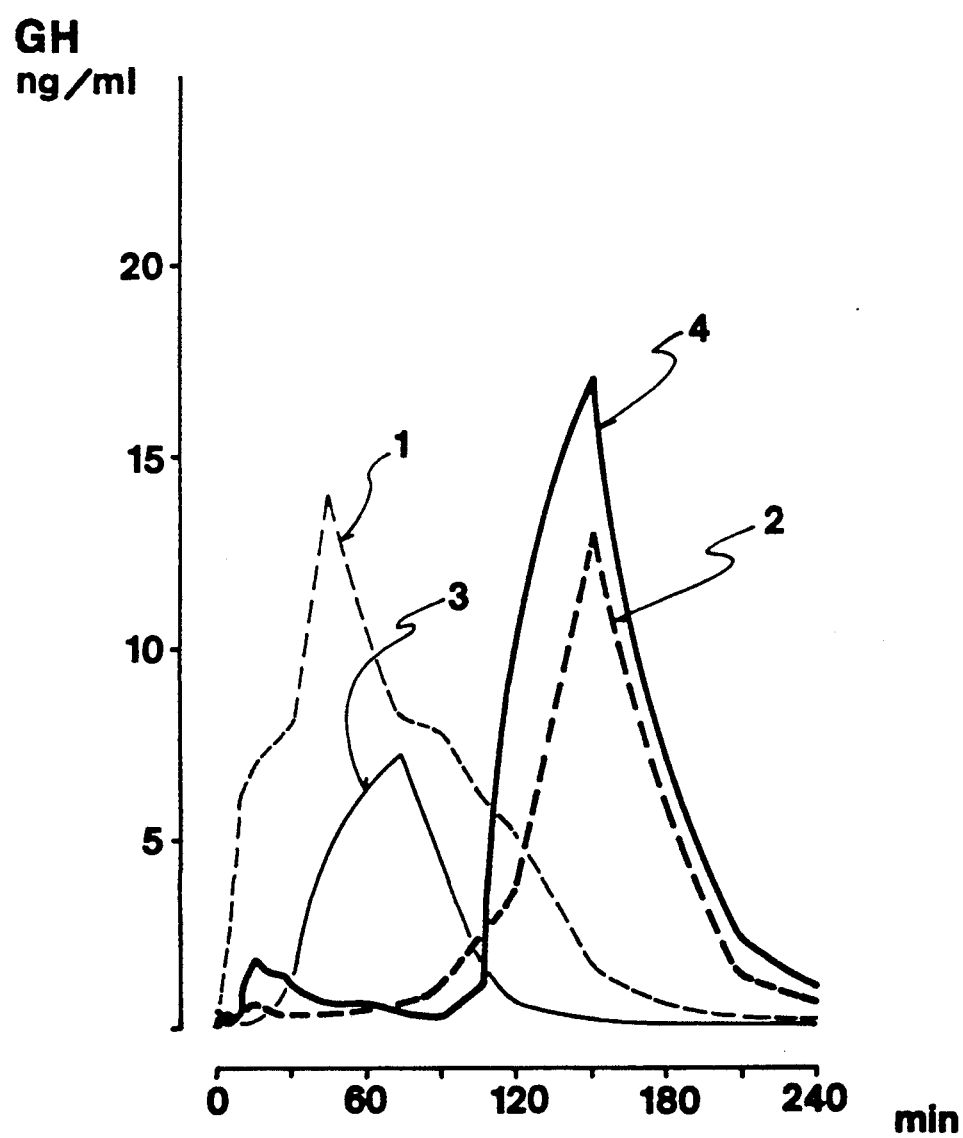

The results of the clinical trials are given in the diagrams of the accompanying FIGS. 1, 2, 3 and 4, of which FIGS. 1 and 2 relate to children and FIGS. 3 and 4 relate to adults. In said diagrams the vertical axis represents the hematic GH content expressed in ng/ml and the horizontal axis represents the blood withdrawal time in minutes.

The curves are indicated by the numbers 1, 2, 3 and 4, these relating to the aforesaid administration scheme. From these curves it can be seen that the compositions containing GHRH and neostigmine according to the invention evoke a GH response which can be practically superimposed on that of intravenous GHRH administration, and decidedly better than that obtained by intranasal administration of an equal dose of GHRH alone.

Moreover, the GHRH and neostigmine compositions according to the invention when administered intranasally are advantageous in the diagnosis of hypophyseal functionality with regard to the determination of GH release by the hypophysis in response to the stimulus of GHRH, and thus allow a more directed and rational approach in the treatment of growth disorders.

We claim:

1. A pharmaceutical composition for intranasal administration suitable for the treatment of growth disorders and the diagnosis of hypophyseal functionality, comprising therapeutically effective quantities of GHRH, a cholinergic agonist and optionally a bile salt, together with pharmaceutically acceptable non-toxic excipients for intranasal administration.

2. A composition as claimed in claim 1, characterised by being in the form of a nasal powder, nasal suspension, nasal ointment, nasal cream, nasal solution, nasal gel, sustained release gel, nasal droplets, nasal atomisation or nasal spray.

3. A composition as claimed in claim 1, characterised in that said cholinergic agonist is methacholine, carbachol, bethanecol, arecholine, pilocarpine, muscarine, acyclidine, oxotremorine, physostigmine, neostigmine, edrophonium, pyridostigmine, demecarium, ambenonium and their salts.

4. A composition as claimed in claim 1, characterised in that said bile salt is an alkaline salt of glycocholic acid, glycochenodeoxycholic acid, taurocholic acid, taurochenodeoxycholic acid, deoxycholic acid, chenodeoxycholic acid, ursodeoxycholic acid or glycodeoxycholic acid.

5. A composition as claimed in claim 1, characterised by being isotonic.

6. A composition as claimed in claim 1, being water-based and containing from 0.01 to 0.75% by weight of GHRH, from 0.15 to 7.5% by weight of cholinergic agonist and optionally from 0.5 to 5% by weight of bile salt.

7. A composition as claimed in claim 1, being halogenated hydrocarbon propellant-based and containing from 0.01 to 1.0% by weight of GHRH, from 0.3 to 4.0% by weight of cholinergic agonist and optionally from 0.5 to 5% by weight of bile salt.

8. A composition as claimed in claim 1, being gelled matrix-based and containing from 0.2 to 1.5% by weight of GHRH, from 1.5 to 7.5% by weight of cholinergic agonist and optionally from 0.5 to 5% by weight of bile salt.

9. A composition as claimed in claim 1, in the form of an oil/water or water/oil emulsion and containing from 0.2 to 1.5% by weight of GHRH from 1.5 to 7.5% by weight of cholinergic agonist and optionally from 0.5 to 5% by weight of bile salt.

10. A composition as claimed in claim 1, in the form of powder and containing from 0.4 to 3% by weight of GHRH, from 3 to 15% by weight of cholinergic antagonist and optionally from 0.5 to 5% by weight of bile salt.

11. A composition as claimed in claim 1, characterised by being administered in a dose consisting of from 3 to 60 $\mu$g/kg of body weight for the GHRH, from 20 to 100 $\mu$g/kg of body weight for the cholinergic agonist and optionally from 10 to 50 $\mu$g/kg of body weight for the bile salt.

* * * * *